United States Patent [19]

Kambara et al.

[11] Patent Number: 5,062,942

[45] Date of Patent: Nov. 5, 1991

[54] FLUORESCENCE DETECTION TYPE ELECTROPHORESIS APPARATUS

[75] Inventors: Hideki Kambara, Hachioji; Tetsuo Nishikawa, Itabashi; Tomoaki Sumitani, Hachioji; Keiichi Nagai, Higashiyamato; Yoshitoshi Ito, Ome, all of Japan

[73] Assignee: Hitachi, Ltd., Tokyo, Japan

[21] Appl. No.: 506,986

[22] Filed: Apr. 10, 1990

[30] Foreign Application Priority Data

Apr. 12, 1989 [JP] Japan .................................. 1-90843
Apr. 12, 1989 [JP] Japan .................................. 1-90845
Aug. 28, 1989 [JP] Japan .................................. 1-218582

[51] Int. Cl.$^5$ .......................................... G01N 27/26
[52] U.S. Cl. ............................ 204/299 R; 204/182.8; 250/458.1; 250/461.1; 250/461.2; 356/344
[58] Field of Search ............... 204/180.1, 182.8, 299 R; 250/458.1, 459.1, 461.1, 461.2; 356/344

[56] References Cited

U.S. PATENT DOCUMENTS 4,832,815  5/1989  Kambara et al. ............... 204/299 R
4,881,812  11/1989  Ohkubo et al. .................. 204/299 R

OTHER PUBLICATIONS

"Nature", vol. 321, 1986, pp. 674–679.

*Primary Examiner*—T. Tung
*Assistant Examiner*—David G. Ryser
*Attorney, Agent, or Firm*—Pennie & Edmonds

[57] ABSTRACT

In a fluorescence detection type electrophoresis apparatus, comprising an electrophoresis separation gel plate (2, 102, 205), an excitation laser beam source (3, 201, 201) for emitting fluorescent light, and a fluorescent light detector (9, 109, 212) for detecting the emitted fluorescent light, a fluorescent light images are divided into a plurality of virtual images by an image divider (5, 7$_2$, 104, 105, 209) and at the same time, the lights corresponding to the individual divided images are wavelength-selected by bandpass filters (8, 8$_3$, 107, 108, 120, 227–230), thereby providing highly accurate, sensitive separation and detection of DNA fragments and the like and determination of base sequence of DNA and the like.

25 Claims, 7 Drawing Sheets

FLUORESCENCE DETECTION TYPE ELECTROPHORESIS APPARATUS

BACKGROUND OF THE INVENTION

The present invention relates to a fluorescence detection type electrophoresis apparatus, particularly to a multicolor fluorescence detection type electrophoresis apparatus. More specifically, the present invention relates to the multicolor fluorescence detection type electrophoresis apparatus, preferably for determining DNA base sequence of DNA or the like in a way that a plurality of fluorophores of different emission wavelengths are used to label in multicolor the fragments of the DNA or the like to be determined for the base sequences. Each of the fluorescent lights of the DNA fragments emitted after electrophoresis separation then can be detected.

Conventional technique of determining the DNA base sequence is autoradiography in which a radioactive isotope element is used for labeling. However, it is not until recently that a fluorescent label technique is used to optically and automatically detect the DNA fragments to automatically determine the DNA base sequences. This technique uses a method in which four DNA fragments of different terminal species are labeled with respective fluorophores of different emission wavelengths, and the DNA fragments are separated by gel electrophoresis. The DNA fragments are irradiated by laser beam on the migration lanes. The fluorescent lights emitted are received by a detector having four respectively selecting bandpass filters lights of said different emission. A conventional detector of the photomultiplier type having four bandpass filters on a rotary plate is moved synchronously with a scanning laser beam as disclosed for example in "Nature", vol. 321, 1986, pp. 674-679.

There is an alternative technique in which a laser beam is applied on an electrophoretic plate in line and the emitted fluorescent light line image is divided through a prism into spectra, which in turn are detected by a highly sensitive, two-dimensional detector as disclosed, for example, in U.S. Pat. No. 4,832,815.

It is important to achieve a high sensitivity in the fluorescent light detector mentioned above. In the fluorescence measuring system where the detector employing a rotary filter scans with the irradiation scanning beam, the proportion of the measuring time, $\alpha$, for one measuring point of gel is expressed by $$\alpha = d/4l$$

where $l$ denotes a length of the measuring area, and $d$ denotes a width of the irradiating laser beam. In general, as $d$ is 0.2 to 0.3 mm and $l$ is longer than or equal to 100 mm, $\alpha$ is smaller than or equal to $10^{-3}$. This is disadvantageous in that it leads to an amount of reception light as low as 1/1000 of the continuous light irradiation and reception method, resulting in a sensitivity that is too low.

On the other hand, in the technique where a laser beam travels through a side end surface of the slab gel to continuously irradiate every measuring point, the fluorescent light images obtained are divided into spectra through a prism, which in turn are detected by a two-dimensional detector. The amount of light reception in this instance is high and resolve the difficulty mentioned above. However, the wavelength dispersion by the prism is not enough to separate lights from different fluorescent dyes. Further, even a slightest position shift of the prism or the lens affect the wavelength separation. That is, a shift of the prism or the lens shifts the position of the image to be detected. Moreover, the light from each fluorescent dye have a wide spectra, although emitted wavelengths from dyes are different only by 20 nm or so at the maximum wavelengths, in many cases. Consequently, it is very difficult to identify different fluorescent dyes, even if the prism is of an optimum quality, and hence, it is difficult to identify with precision the DNA base species using this technique.

As pointed out above, the conventional techniques are disadvantageous in that they lack a high sensitivity and a precision for separating wavelength.

SUMMARY OF THE INVENTION

An object of the present invention is to dissolve the difficulties mentioned above, and to provide a multicolor fluorescence detection type of a highly sensitive electrophoresis apparatus that is capable of separating and detecting DNAs with a great precision.

The inventors, as a result of their study, found that DNAs can be separate and detected with a great precision by dividing a fluorescent light image obtained by applying a laser beam on an electrophoresis separation plate into a plurality of virtual images. The individual divided image lights are then selected according to the wavelength by passing through bandpass filters. These resulting images are then placed on a detector for separation and detection. They further continued the study on the basis of the new knowledge and completed the present invention.

Therefore, the fluorescence detection type electrophoresis apparatus of the present invention comprises at least an electrophoresis separation gel plate, an excitation laser beam source for emitting fluorescent light, and a fluorescent light detector for detecting the emitted fluorescent light, and is characterized in that the fluorescence detection type electrophoresis apparatus has an image dividing means of a linear fluorescent light image obtained by applying a laser beam to the electrophoresis separation gel plate, has bandpass filters of different transmission wavelengths, same as the divided images in number, corresponding to the images divided by the image dividing means and has an optical means for focusing on the fluorescent light detector the individual fluorescent line images of different transmission wavelengths formed through the respective bandpass filters.

In a practical construction of the fluorescence detection type electrophoresis apparatus of the present invention, the laser beam irradiation on the the electrophoresis separation gel plate is directed toward and penetrates through a slab gel of the electrophoresis separation gel plate in parallel with the electrophoresis separation gel plate through the side end surface of the gel plate, and a fluorescent light line image obtained by the laser irradiation is along with a path of the laser beam in the slab gel.

The image dividing means can comprise a prism or prisms added between the laser beam irradiated portion and the fluorescent light receiving portion; can comprise a plurality of reflection mirrors arranged in parallel with an axis of a laser beam in the electrophoresis separation gel plate; or can comprise at least a plurality of lenses of different optic axes or a lens divided into fragments of different optic axes, being provided on a path on which fluorescent lights emitted from a laser beam irradiated portion of the electrophoresis separation gel plate come to the focusing position on the fluorescent light detector. Further, the image dividing means can comprise an additional prism or mirror for dividing the fluorescent light image on a path on which fluorescent lights emitted from a laser beam irradiated portion of the electrophoresis separation gel plate come to the focusing position on the fluorescent light detector to help the image dividing function of the image dividing means mentioned above.

The plurality of the lenses of different optic axes mentioned above can be provided by overlapping two or four rectangular condenser lenses in the vertical direction with their longer sides laid horizontally.

With respect to providing the single lens that is divided into fragments having deviated optic axes mentioned above, for example, a circular condenser lens can be radially divided into two or four fragments on a line or lines drawn through a center thereof, and the fragments can be integrated with each inclined 1 to 2 degrees from a plane at right angles to the optic axis of the original lens.

To realize the image dividing function of the image dividing means, for example, the additional prism or mirror can be arranged as follow. Two mirrors of 10 mm by 100 mm are bonded together on their longer side edges in the state in which the mirrors are deviated from a plane by about 1 degree. The integrated mirror can be put in position 5 to 10 mm behind the laser beam irradiated portion. The prism of 150 degrees vertex can be put in position 20 mm in front of the laser beam irradiated portion with its edge being in parallel with the irradiated portion.

If the iamge dividing means is comprised of a plurality of reflection mirrors, a corresponding number of bandpass filters of different transmission wavelengths are provided on the respective fluorescent light paths from the reflection mirrors to focusing positions on a fluorescent light detector.

Preferably, the plurality of the reflection mirrors are arranged on the circumference of an ellipse having a point of the laser beam within the electrophoresis separation gel plate as one center thereof.

For practical use, for example, the plurality of the reflection mirrors can be arranged in a way that four mirrors of 10 mm by 100 mm are bonded together on their longer side edges with the four bends to make contact with the ellipse.

Further, the image division can be made with use of prism for accomplishment of the object of the present invention. First, the fluorescent image obtained by applying the laser beam on the electrophoresis separation plate is divided into a plurality of virtual images employing a prism. Each of the divided virtual images is then wavelength-dispersed through bandpass filter to make the image focus on the detector to detect the separated images for achieving the object of the present invention.

In that case, the fluorescence detection type electrophoresis apparatus comprising at least an electrophoresis separation gel plate, a laser beam source, and a fluorescent light detector, has a prism having a plurality of light-outgoing planes for dividing a fluorescent light line image obtained by applying a laser beam to an appropriate position of the electrophoresis separation gel plate and has an optical system for individually focusing on the fluorescent light detector a plurality of the fluorescent line image divided through the plurality of the light-outgoing planes of the prism.

The optical system has a bandpass filter of individually different transmission wavelengths, which is provided on corresponding paths of the divided image lights coming out of the plurality of the light-outgoing planes of the prism.

The prism can be a polyhedron which is symmetrical with a section including edges of a center vertex or a polyhedron like trapezoid which is symmetrical with a center section.

The prism needs to be made of a material of a high refraction index, such as BaF01, LaF3, or SF3 glass, particularly in the multicolor fluorescence detection type electrophoresis apparatus of the present invention.

The prism can be preferably positioned in a way that at least one edge of the prism is in a plane including a fluorescent light line obtained as a result of a laser beam irradiation to the electrophoresis separation plates and a center of the focusing position of the fluorescent light detector, and is in parallel with the fluorescent light line, or in any other manner in which the prism is symmetric up and down with respect to a plane including fluorescent light line images obtained as a result of laser beam irradiation to the electrophoresis separation plates and a center of the focusing position of the fluorescent light detector, and a vertex of the prism at the center is in parallel with the fluorescent light line images. The prism can be provided at any position between the electrophoretic plate and bandpass filter.

The object of the present invention can be accomplished well in a way that in the multicolor fluorescence detection type electrophoresis apparatus, devices for image-dividing and wavelength-selecting the fluorescent light image can partly include a cylindrical convex lens and a cylindrical concave lens, and the fluorescent lights emitted to a wide angle from the fluorescent light image can be condensed with use of the cylindrical convex lens and can be focused on the light reception plane through the cylindrical concave lens.

In this case, the multicolor fluorescence detection type electrophoresis apparatus comprising at least an electrophoresis separation gel plate, a laser beam source, and a fluorescent light detector, is characterized in that devices for image-dividing and wavelength-selecting the fluorescent light image include a cylindrical convex lens, a cylindrical concave lens, and a bandpass filter.

In that case, also, as the device in practical use for image division, for example, the bandpass filter can be a divided multiplane filter that is a multiplane prism having bandpass filter film on every light-outgoing plane or the portions of the light incidence plane corresponding to the respective light-outgoing planes, thereby allowing image division. In this connection, the divided multiplane filter can be provided between the cylindrical convex lens and a focusing lens. Further, it is preferable that planes of the divided multiplane filter have areas sized so that amounts of the fluorescent lights passing them can be substantially equal.

As another example of the device for image division, the cylindrical convex lens comprises a plurality of divided cylindrical convex lenses, by which the fluorescent light image can be divided.

Furthermore, it is preferable that to prevent the light emission from portions other than the emission point by laser irradiation from interfering measurement, a slit is provided in parallel with fluorescent light line images between an emitting point of the fluorescent light line images and a cylindrical convex lens to cut out upper and lower parts of the fluorescent lights emitted from the emitting point higher or lower than specific angles.

Moreover, it is preferable that a width of the slit is made narrower than an interval of virtual object positions.

In case that the fluorescence detection type electrophoresis apparatus of the present invention is used as multicolor fluorescence detection type electrophoresis apparatus for separation and detection of multicolor-labeled samples, the separation and detection sample used for migrating in the electrophoresis separation plate is a multicolor-labeled sample. The fluorophores used for multicolor labeling are FITC (Fluorescein isothiocyanate) of 515 nm emission wavelength, NBD-F (4-fluoro-7-nitrobenzofurazan) of 540 nm emission wavelength, TRITC (tetramethyl rhodamine isothiocyanate) of 573 nm emission wavelength, and Texas Red of 610 nm emission wavelength.

The bandpass filter used in connection with the multicolor labeling is a multilayer dielectric filter or the like of 20 to 40 nm transmission wavelength width, the center wavelength of which coincides with the emission wavelength. It also may be a combination of a dielectric evaporated multilayer filter and a color glass filter.

The fluorescent light detector used is normally a two-dimensional fluorescent light detector.

As the samples for separation and detection employing the fluorescence detection type electrophoresis apparatus of the present invention, there can be shown DNAs or RNAs of which the base sequences are to be determined. There can be shown also proteins and the like. Further, it can be used for a human gene diagnosis apparatus.

The fluorescence detection type electrophoresis apparatus of the present invention, as described above, can be most preferably used as multicolor fluorescence detection type electrophoresis apparatus. It also can be used for the detection of monocolor fluorescences. In this case, also, the fluorescence detection type electrophoresis apparatus of the present invention provides an advantage that accurate separation and detection can be achieved as the possible measurement errors due to the change of the measurement conditions such as fluctuation of the laser beam irradiation of the fluorescence detection type electrophoresis apparatus can be compensated. This can be done with a combined bandpass filter selected so that a fluorescent light line image is divided, for example, into two images, one of which can be used for measuring a peak value of the fluorescent light, and the other is used for measure specific lights of low wavelengths.

As explained above, in accordance with the present invention, the fluorescent image obtained by applying the laser beam on the electrophoresis separation plate is first divided into a plurality of virtual images by the image dividing means comprising the reflection mirror, a plurality of lenses of different optic axes, the divided lens of optic axes deviated each other, prism or the like. Then, the individual divided image lights pass the wavelength dispersion process of bandpass filter to focus on the detector for required separation and detection.

Further, in accordance with the present invention, the devices for dividing the fluorescent image and separating the wavelengths are partly made up of the cylindrical convex lens and cylindrical concave lens. The fluorescent lights emitted to wide angles from the fluorescent light images can be condensed through the cylindrical convex lens, and be focused through the cylindrical concave lens on the light reception plane. This means that the fluorescent lights emitted to wide solid angles from the emission point of each fluorescent light image can be extensively used. The fluorescent lights that were image-divided and wavelength-selected by the devices are focused on different positions of the two-dimensional detector or the like. These signals can be processed to provide high sensitivities of measurements of the DNA fragments.

More specifically, one of the cases where the prism is used as image dividing means will be described below. In the fluorescence detection type electrophoresis apparatus of the present invention, the edge from the vertex of the center portion of the prism is preferably laid overlapped on the line emission portion as looked toward the irradiation portion from the pupil of the light reception lens. The lights the pass the upper and lower parts of the prism can be focused as two images on the two-dimensional detector as if emitted from different points and at the same time, can be wavelength-dispersed upward and downward. The two lights coming out of the respective parts of the prism pass the different filters to the detector. The signals of which the wavelengths are close to each other are allowed for separation and detection by the passing filters different according to the upper or lower part through which the light passes. The signals of large wavelength difference is allowed for dispersion and detection by the prism.

Therefore, using either of the image dividing means mentioned above, the fluorescence detection type electrophoresis apparatus of the present invention can separate and detect the fluorescent lights of different emission wavelengths at a high accuracy and simultaneously without time sharing, that is, in a way that the measurements need not be divided in terms of time.

Accordingly, the apparatus of the present invention can be preferably used for determining the base sequences of the multicolor fluorescence labeled DNA fragments.

Moreover, the fluorescence detection type electrophoresis apparatus of the present invention provides a high amount of reception light to provide a high sensitivity, as the irradiated portions are continuously irradiated through the side end surface, and the two-dimensional detector can observe the whole irradiated area at the same time.

DESCRIPTION OF THE PREFERRED EMBODIMENTS

First Embodiment

Figure 1:
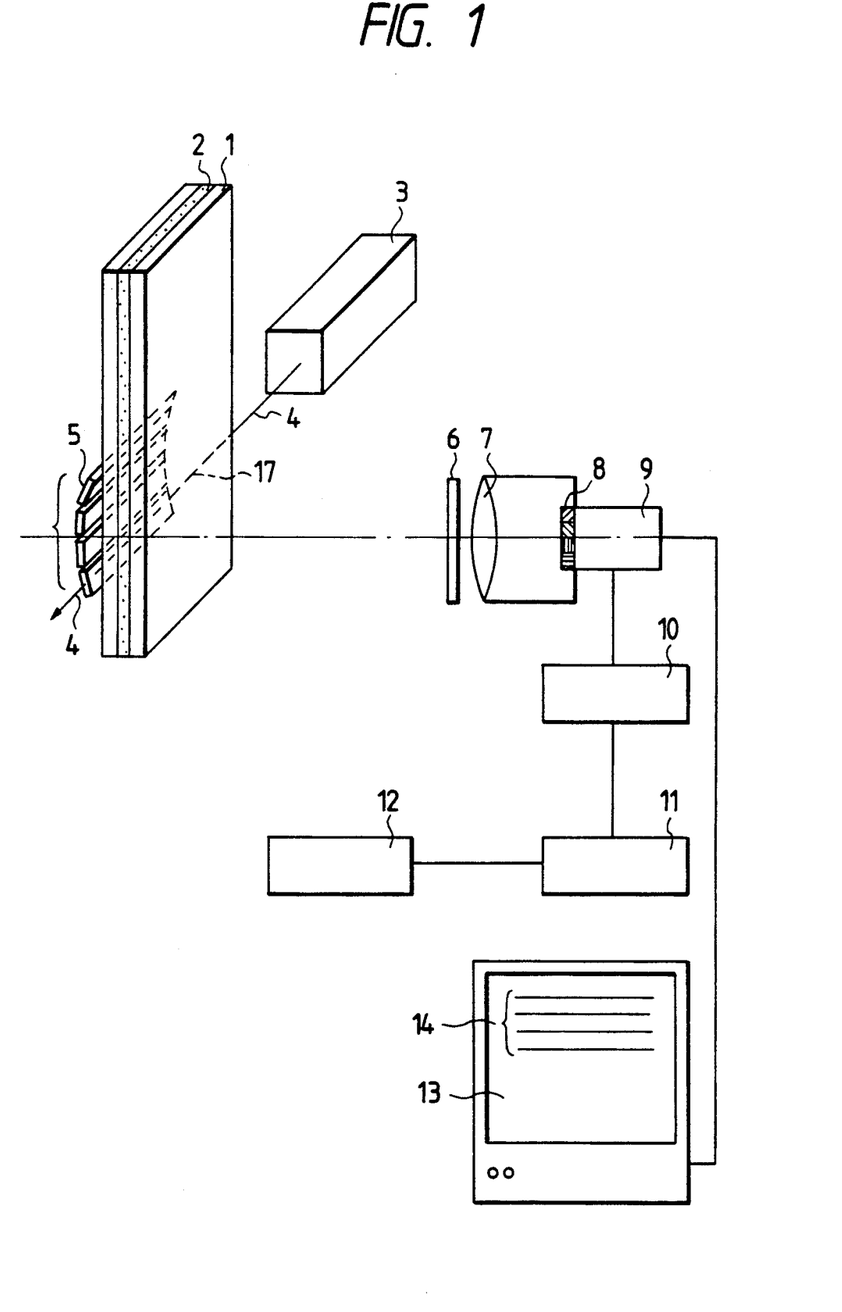
FIG. 1 is a combined block diagram and and a partially perspective view illustrating the fluorescence detection type electrophoresis apparatus in an embodiment of the present invention in which a mirror is used.
Figure 2:
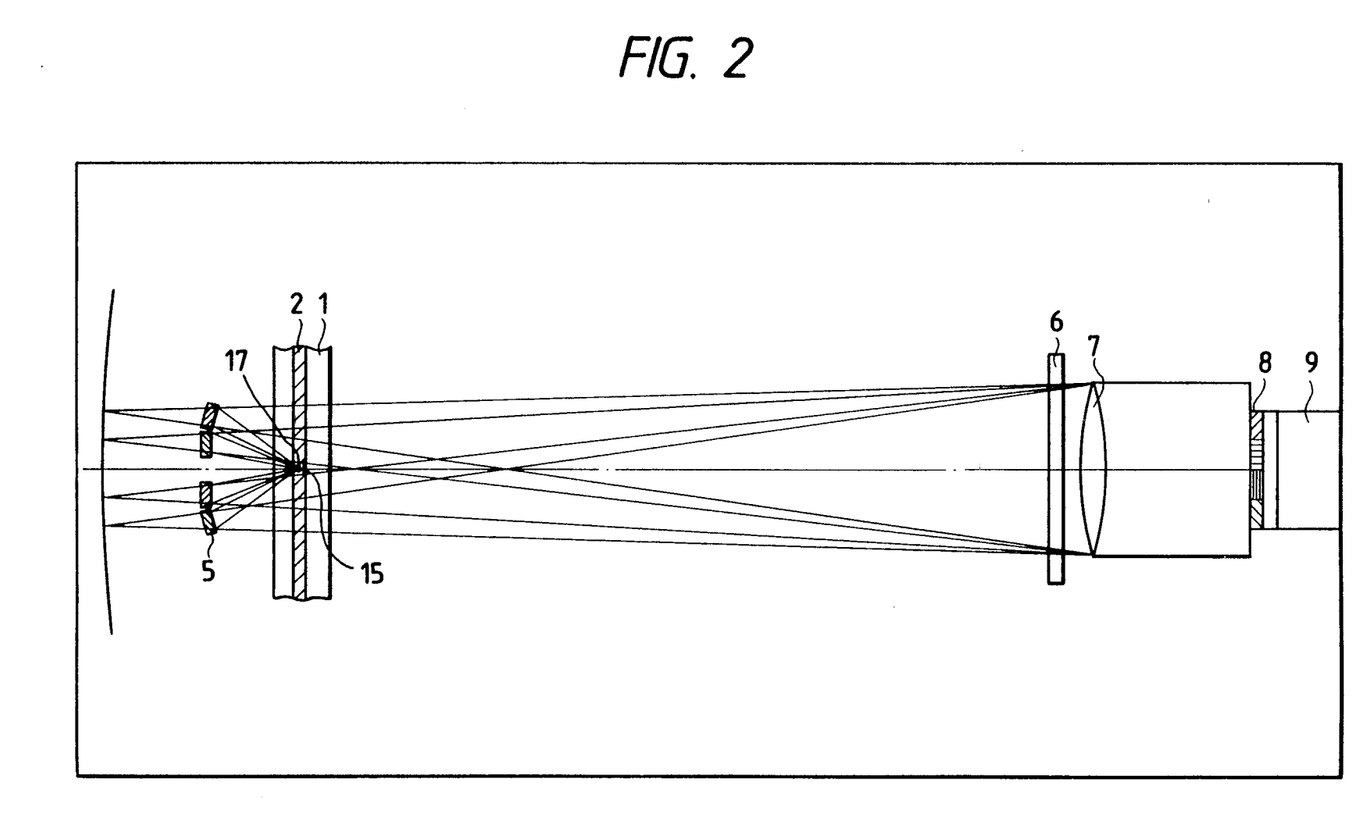
FIG. 2 is a detailed view of a portion of the optical system of the electrophoresis apparatus shown in FIG. 1.

Referring now to FIGS. 1 and 2, a first embodiment of the present invention will be described below.

A laser beam 4 which is generated from an argon laser source 3 of 488 nm wavelength and 10 mW output power, is applied in a slab gel 2 of polyacrylamide of 6% concentration held between two sheets of glass plate or quartz plate 1 each having a dimension of 300 mm by 200 mm by 5 mm, separated 0.3 mm apart, through the side end surface thereof. It should be noted that the concentration of the polyacrylamide is hereinafter indicated as its total monomer concentration in percentage of weight per volume (g/ml). An irradiated portion 17 is indicated as a point in a section view of FIG. 2.

DNA samples labeled with four kinds of color fluorophores for the respective four terminal species are injected into sample injection wells (not shown) on top of the slab gel, and migrate downward. There can be a plurality of migration lanes arranged. In this case, however, the laser beam 4 can irradiate all the migration lanes. A fluorescent light will emit along with the irradiated portion 17. In one of the conventional methods in which a single-color fluorescence label is used to identify the terminal species by difference of the migration lane, a fluorescent light intensity changing with time is observed in a way that the fluorescent line images is focused on a line sensor or two-dimensional detector through a lens having an excitation light cut filter. The four color fluorophores used are the FITC, NBD-F, TRITC, and Texas Red as mentioned previously. Instead of the color fluorophores, a fluorophore of metallic complex can be used. In this example where the four color fluorophores are used, four rectangular mirrors 5 of 1 cm high and 10 cm wide are put in position beyond the electrophoretic plate 2 opposite to the two-dimensional detector 9 to reflect the fluorescent light line images so that four virtual images can be viewed from the detector side. The four mirrors 5 are contiguously arranged in a curved position on a curve having the shape of a circumference of an ellipse of 20 cm major axis with the centers thereof being at a point of a pupil of the lens 7 and a portion of the gel irradiated with the laser beam so that the distances from the detector to the four virtual images are equal to each other. The four virtual images are focused on the two-dimensional detector 9 through the lens 7 as four lines. There are arranged four bandpass filters 8 of 515 nm, 573 nm, 540 nm, and 610 nm transmission wavelengths corresponding to the four fluorophores respectively in front of the focusing position to select the virtual images by wavelengths. Alternatively, the bandpass filters may be positioned at a place between the mirrors and two-dimensional detector 9 instead of the place right before the two-dimensional detector. The images monitored by the two-dimensional detector appear as four lines 14 as shown on a monitor 13. These lines are signals given from the fluorophores of different wavelengths; that is, the signals come from the DNA fragments having different terminal species. The axis of abscissas of the monitor represents a lateral direction of the electrophoretic plates. The signals at the same position of abscissa of the four line images are information of the samples contained on the same migration lane. The signals can be compared one another to determine the terminal species.

FIG. 2 illustrates the details of an optical system of the present embodiment. The fluorescent lights reflected by the four mirrors 5 can form the virtual images on the circumference with the center thereof at the pupil of the lens.

There is a strip reflection mirror 15 of 1 mm wide fitted by evaporation process to the glass plates on the side in contact with the slab gel so as to increase the amount of received lights and at the same time to prevent the fluorescent lights of the irradiated portion from directly coming into the light receiving section. The reflection mirror has an area enough to reflect all the lights that can enter the light receiving section. Alternately, the reflection mirror may positioned at a place between the detector and migration plate. It also can be combined with a mirror having prism to adjust the light path.

In the Figures, a numeral 6 indicates the excitation light cut mirror, numeral 10 a control unit, numeral 11 a data processing unit, and numeral 12 a display.

Second Embodiment

Figures 3A, 3B:
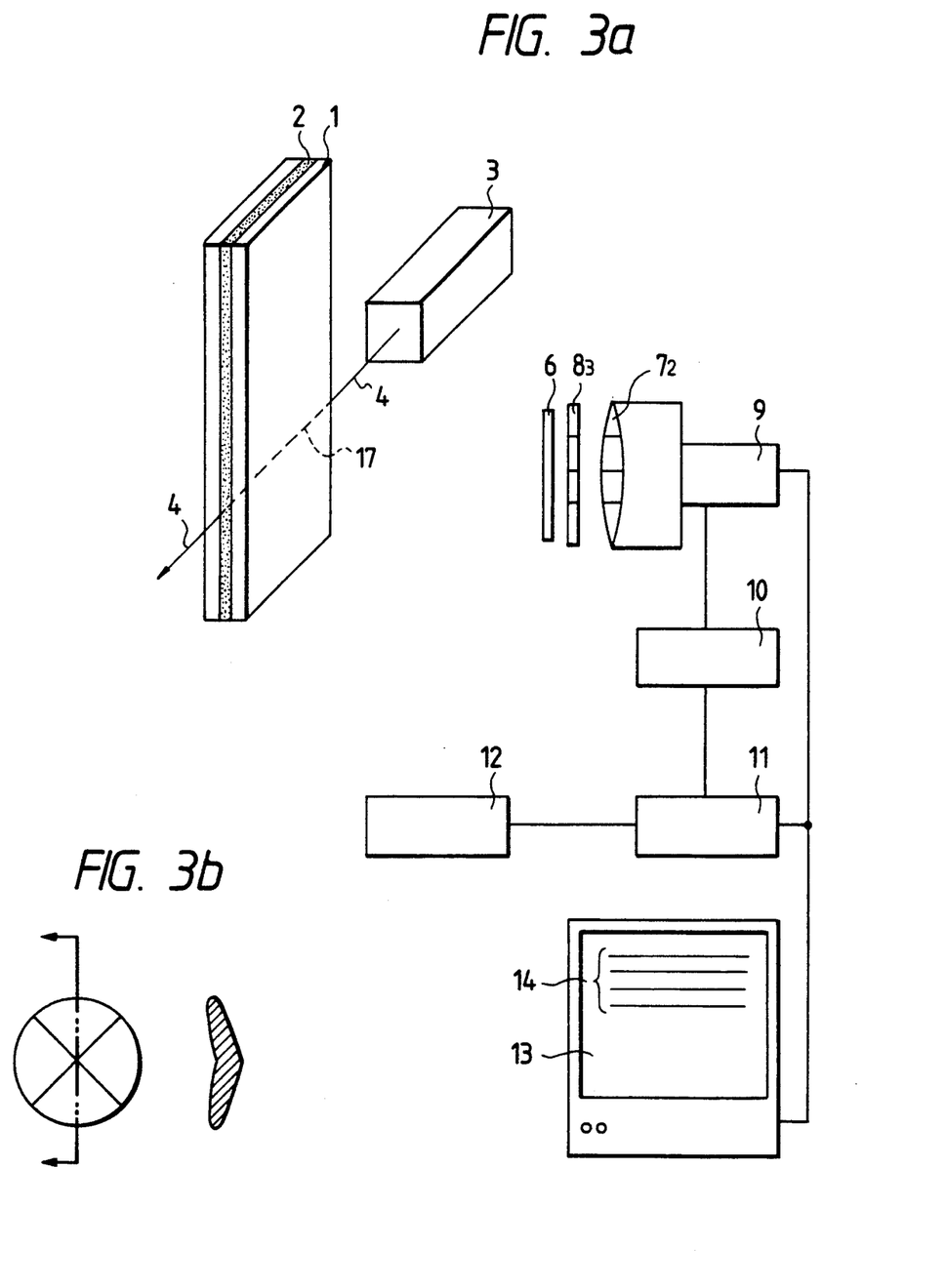
FIG. 3a is a combined block diagram and and a partially perspective view of the fluorescence detection type electrophoresis apparatus in an embodiment of the present invention in which a plurality of lenses of different optic axes is used.
FIG. 3b is a plan detailed view of the four-divided lens of deviated optical axes.

Referring now to FIG. 3a, a second embodiment of the present invention will be described below. A laser beam 4 which is generated from an argon laser source 3 of 488 nm wavelength and 10 mW output power, is applied in a slab gel 2 of polyacrylamide of 6% concentration held between two sheets of glass plate or quartz plate 1 of 300 mm by 200 mm by 5 mm separated 0.3 mm apart, through the side end surface thereof. An irradiated portion 17 is indicated as a point in a section view as in the case of FIG. 2. DNA samples labeled with four kinds of color fluorophores for the respective four terminal species each are injected into sample injection wells (not shown) on top of the slab gel, and migrate downward. One sheet of electrophoretic plate can normally maintain 20 to 30 migration lanes. The laser beam 4 can irradiate all the migration lanes at the same time. A fluorescent light will emit along with the irradiated portion 17.

The DNA fragments labeled with the four fluorophores are separated according to lengths thereof on different migration lanes for the respective samples. The DNA fragments can emit fluorescent lights of various wavelengths according to the kinds of terminal species when passing through the portion at which the laser beam is applied. The emitted lights can be seen along with the irradiated area as line images. If the fluorescent lights are separated into spectra with use of a prism, the respective signals cannot be separated sufficiently because of too little wavelength dispersion. Bandpass filters are advantageous for separating the fluorescent light wavelengths. In this embodiment, as shown in FIG. 3a, four-lens means $7_2$ of different optic axes is used to divide the images to obtain a quadruple fluorescent image, with a bandpass filter means $8_3$ put in position in front or behind the lenses $7_2$. The said four-lens means $7_2$ is made of four rectangular lenses arranged in parallel with longitudinal edges thereof bonded together, the optic axes being made different from each other.

The bandpass filter $8_3$ used in this embodiment is a mosaic filter made of a multilayer dielectric material same as in the bandpass filter mentioned before. Alternatively the bandpass filter $8_3$ may be put in front surface of the respective lenses of the four-lens means $7_2$.

The images monitored on the two-dimensional detector is like the one shown by the numeral 14. Portions corresponding to the respective lines to be observed are read out and compensated by a correction calculation of light intensities to obtain light intensity changes of the respective DNA fragments.

Alternatively, the four-lens means $7_2$ made of four lenses of different optic axes shown in FIG. 3a may be replaced with a divided lens means as shown in FIG. 3b. The divided lens means is, is made in a way that a lens is divided radially into four lens fragments, which are reformed with optical axes thereof deviated from each other. In this case, the bandpass filter means must be radially made according to the structure of the divided lens. Additionally, for dividing the image in this embodiment, a reflection mirror or prism may be used together with the divided lens mentioned above.

Third Embodiment

Figure 4:
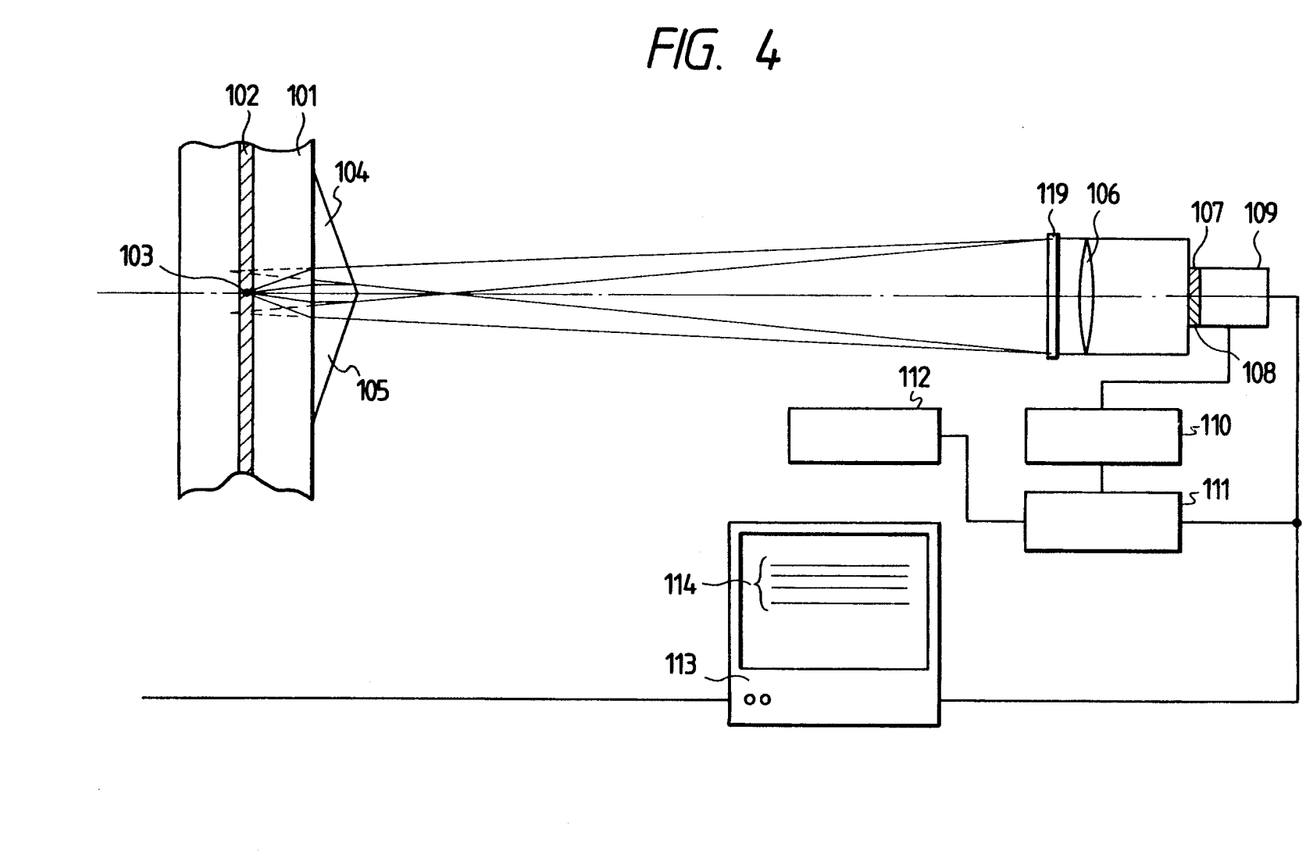
FIG. 4 is a combined block diagram a view of the fluorescence detection type electrophoresis apparatus in an embodiment of the present invention in which a prism is used.
Figure 5:
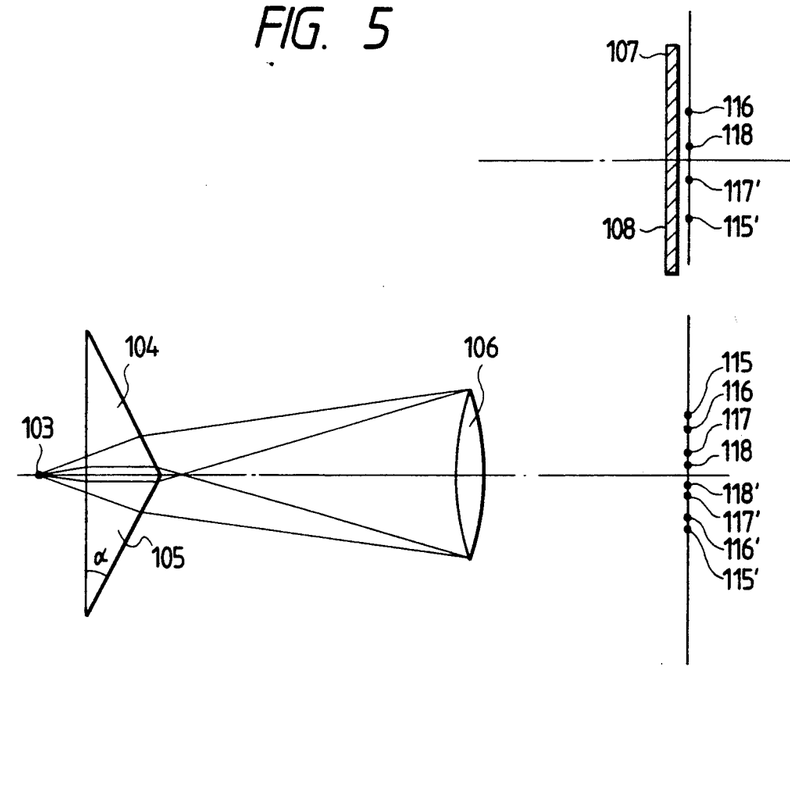
FIG. 5 is a detailed view of a portion of the optical system of the fluorescence detection type electrophoresis apparatus shown in FIG. 4.

Referring now to FIGS. 4 and 5, a third embodiment of the present invention will be described below. FIG. 4 is a schematic view of the electrophoresis apparatus of the present embodiment. The optical system is shown in section. An argon laser of 488 nm wavelength and 10 mW output power is applied in a slab gel 102 of polyacrylamide of 6% concentration held between two sheets of glass plate or quartz plate 101 of 300 mm by 200 mm by 5 mm separated 0.3 mm apart, through the side end surface thereof. An irradiated portion 103 is indicated as a point in the section view. A light outgoing upward out of the irradiated portion is refracted through an upper prism 104, and then is focused through a lens 106 on a lower side of a two-dimensional detector 109. On the other hand, a light outgoing downward is refracted through a lower prism 105, and then is focused through the lens 106 on an upper side of the two-dimensional detector 109. In this embodiment, DNA fragments as samples for fluorescent detection are fluorescence-labeled with fluorophores of four different wavelengths corresponding to four kinds of terminal species, including FITC (fluorescein isothiocyanate) of 515 nm emission wavelength, NBD-F (4-fluoro-7-nitrobenzofurazan) of 540 nm emission wavelength, TRITC (tetramethyl rhodamine isothiocyanate) of 573 nm emission wavelength, and Texas Red of 610 nm emission wavelength. Accordingly, four lights of the wavelengths mentioned above are emitted from the emission point, and are dispersed through the prisms. The dispersed lights, as shown in FIG. 5, can produce four lines (four points in the section view) on each of the upper and lower sides. Numerals 115 and 115', 116 and 116', 117 and 117', and 118 and 118' indicate images of the same wavelengths respectively, corresponding to the lights passing through the lower and upper prisms. More specifically, the numerals 115 and 115' indicate the light images emitted from the Texas Red, 116 and 116' denote the ones from the TRITC, 117 and 117' denote the ones from the NBD-F, and 118 and 118' denote the ones from the FITC. In this example, the light images 115 and 116 and the ones 117 and 118 cannot be sufficiently identified from each other respectively by wavelength dispersion by prism due to little wavelength difference. The light images 115 and 117 and the ones 116 and 118, however, can be identified well from each other respectively. The bandpass filter has the upper side 107 of two transmission wavelengths, 515 nm and 573 nm, provided, and has the lower side 108 of two transmission wavelengths, 540 nm and 610 nm provided, thereby allowing identification of four colors. FIG. 5 illustrates such a fashion as above. If the filters are not provided, with an excitation light cut filter 119 provided, the two-dimensional detector will monitor eight lines; however, adjacent lines of them cannot be clearly separated. If the filters 107 and 108 are attached, the four lines can be separated from each other to detect. (See the upper right view of FIG. 5 and the monitor picture of FIG. 4.) The signals obtained through the four fluorescent light images can be independently read out with use of one to three horizontal scanning lines of the two-dimensional detector. The signals obtained can be converted to information of four terminal species of the DNA fragments using a data processing unit 111 to determine DNA base sequences.

In this embodiment, the prisms 104 and 105 are integrated together, with a narrow vertex thereof made 30 degrees of angle α. A material used for the prisms is BaF glass. The vertexes of the prisms are determined so that the lights passing through thick portion of the prism 104 can be refracted to pass below a lower edge of the lens 106. This allows the lights of solid angle, that the lens can look, to enter the lens.

Alternatively, in this embodiment, the prisms 104 and 105 may be put at another position between the electrophoretic plate and two-dimensional detector.

In FIG. 4, numeral 110 indicates a control unit, 113 a monitor, and 114 line images.

Fourth Embodiment

Figure 6:
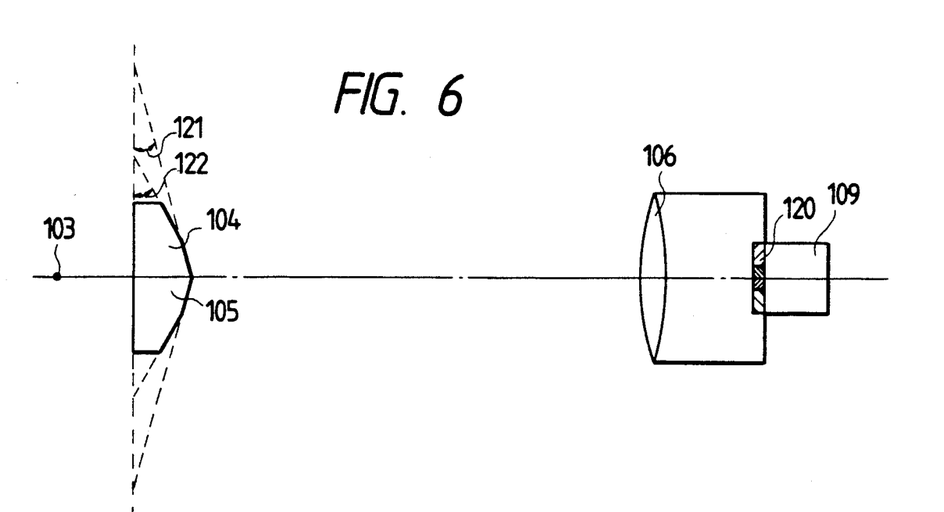
FIG. 6 is a detailed view of the optical system of the fluorescence detection type electrophoresis apparatus in an embodiment of the present invention in which a multiplane prism is used.

FIG. 6 shows an example in which a polyhedron prism means is used. A light emitted from an emission point 103 can be passed through an upper prism 104 or a lower prism 105, and can be focused on different positions of a two-dimensional detector 109 by a lens 106. If each of the upper prism 104 and the lower prism 105, as shown, has two surfaces of different angles, the lights passing through the upper and lower prisms are focused on the detector 109 as two images each, four images in total. Though the number of the images increases, an overall light reception solid angle becomes larger as viewed through the prisms, and, thus, amount of light for each detected fluorescent light image will hardly change as compared with that of the case where no prisms are used. There are filters 120 of different transmission wavelengths put at the respective image-focused positions or right behind the prisms 104, 105 to separate the wavelengths to detect signals. As bandpass filters provide a sharp cutting of transmission waves, they can separate the wavelengths at a higher accuracy than the prisms which disperse them for separating wavelengths. A material used for the prisms in this embodiment is BK5. Angles 121 and 122 of the prisms are 15 and 30 degrees, respectively.

Fifth Embodiment

Referring now to FIGS. 7 through 10, a fifth embodiment of the present invention will be described below.

Figure 7:
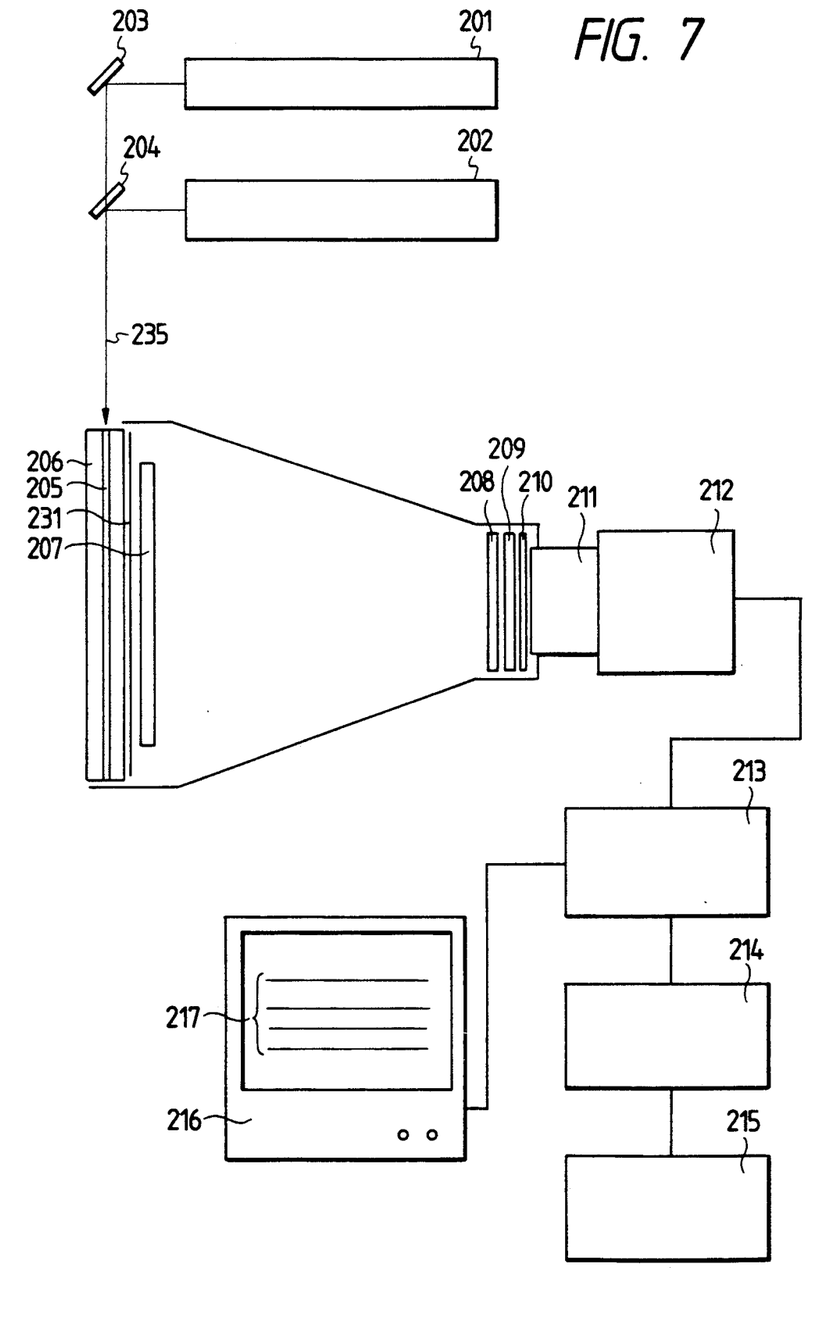
FIG. 7 is a schematic view of the fluorescence detection type electrophoresis apparatus in an embodiment of the present invention in which cylindrical lenses are used.
Figure 8:
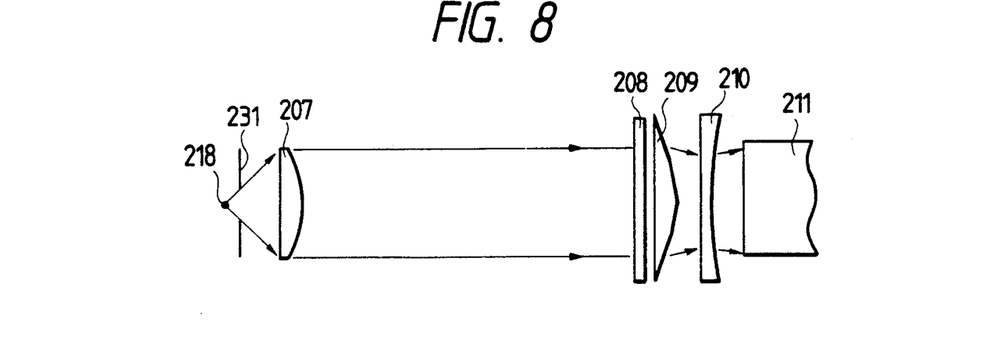
FIG. 8 is a detailed view of a portion of the system of the fluorescence detection type electrophoresis apparatus shown in FIG. 7.
Figure 9:
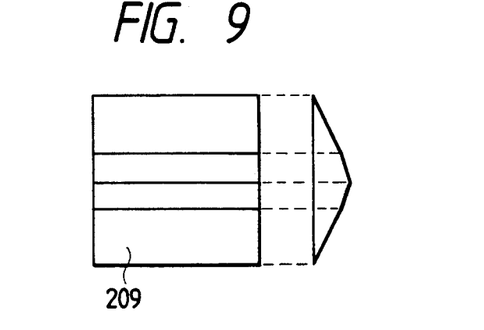
FIG. 9 is a set of plan and side views of the four-divided filter used in the optical system shown in FIG. 8.

Labeling fluorophores used in this embodiment are Texas Red of 605 nm emission wavelength and three kinds of phthalocyanine fluorophore of 680 nm, 703 nm, and 725 nm emission wavelengths. For exciting the former fluorophore, a He-Ne laser 201 of 543 nm wavelength is used, and for exciting the latter three a He-Ne laser 202 of 633 nm wavelength is used. Lights radiated from the both lasers can be superimposed by mirrors 203 and 204 to form a laser beam 235. The laser beam 235 then can be focused through a lens (not shown) and irradiate in a gel electrophoresis plate (slab gel) 205 through the side end surface thereof. The slab gel is 0.3 mm thick, and is held by quartz or glass plates 206. The slab gel has a width of 200 mm. The center portion of the slab gel 120 mm width, is used for analysis. The fluorescent light emitted out of the irradiated portion passes through a slit 231, and then its components dispersing up and down and perpendicularly to the irradiation laser beam are condensed through a convex cylindrical lens 207 to parallel lights. As the convex cylindrical lens 207 magnifies a solid angle of light reception eight times in the up and down direction, it provides a high sensitivity. The slit 231 of 5 mm intervals is put at a position 5 mm apart from the light emitting portion. This prevents the fluorescence emitted by the scattered light from interfering measurement. The fluorescence emitted by the scattered light occurs when a large amount of labeled DNA is migrating and passing through portions other than the one to which the laser beam is applied. There is provided a scattering light cut filter 208, comprising a color glass filter and a total reflection mirror for the lights of excitation wavelengths, which allows the fluorescent lights emitted from the four kinds of fluorophores to pass only. The fluorescent lights passed are spatially selected in terms of wavelengths to outgo through a four-divided multiplane filter 209 which has four light-outgoing planes laid on the different planes respectively as shown in FIG. 8. Alternatively, the multiplane filter 209 may be replaced by a plurality of cylindrical lenses that are arranged up and down with different vertical angles. The separated fluorescent lights are compensated directionally through a cylindrical concave lens 210 so that vertical focusing positions thereof can be aligned with horizontal positions thereof. Then, they are focused on a two-dimensional detector 212 through a focusing lens 211, Fuji Optical Instrument Inc.'s CF25L, of 25 mm focal length and 0.85 F. The four-divided filter 209, as shown in FIGS. 8 and 9, is constructed such that the light-outgoing plane is divided to four planes. Each planes has a bandpass filter of dielectric multilayer film of a specific transmission wavelength different from each other evaporated. Division of the light-outgoing planes is designed to provide 5 mm or more intervals of virtual images. The cylindrical convex lens 207 used in this embodiment is of 22 mm focal length, 22 mm high (vertical width), and 120 mm wide (horizontal width) to provide a parallel beam of 22 mm in vertical width. As to the vertical components of the fluorescent lights, the fluorescent light beams are made perpendicular to the filter through the cylindrical convex lens 207 to provide a higher filtration accuracy.

Figure 10:
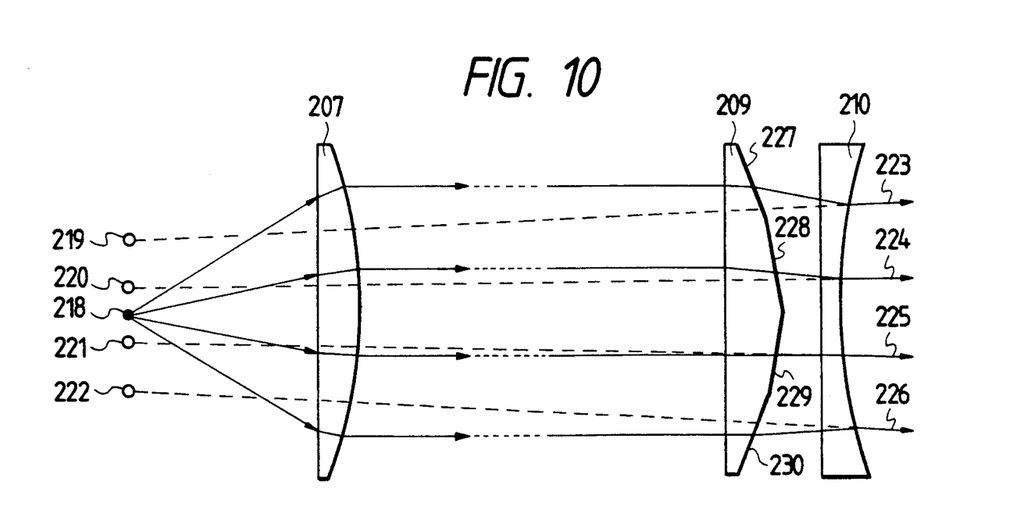
FIG. 10 is a schematic view showing an image focusing characteristic of the optical system including the four-divided filter.

The divided filter 209 is of 30 mm long and 30 mm wide, or being able to form a circle of 30 mm diameter. Areas of the divided filters through which the lights can pass is adjusted so that the amount of lights passing the filter planes can be virtually equal. The widths of filter sections of the divided filter, as shown in FIG. 9, are 10 mm, 5 mm, 5 mm, and 10 mm as measured below tops thereof. Each planes of the divided filter is arranged so as to be parallel with the respective emission lines. As every filter plane is not on the same plane, the two-dimensional detector 212 will show four fluorescent line images. A deviation, x, of each fluorescent line image from the origin depends on an angle, $\theta$, made between the neighboring light outgoing planes of the filter and a distance, l, from an object point 218 to the filter. The deviation, x, can be approximately expressed with use of a diffractive index, n as $x \approx l \tan (n-1) \theta$. The fluorescent lights passed through the respective planes 227, 228, 229, and 230, as shown FIG. 10, are changed outward in the propagation direction as indicated by light paths 223, 224, 225, and 226. The lights are focused as if there are object points at positions 219, 220, 221, and 222. In this embodiment, because $l=150$ mm and $\theta=4$ degrees, the resulting deviation, x is 6 mm. As the intervals of the slit 231 is 5 mm, the images passed through the filter planes will not be superimposed with their peripheral satellite images, so that the measurement will not be prevented. That is, angles made from the fluorescent light incidence plane of the divided filter to the light-outgoing planes are selected for 6 degrees, 2 degrees, 2 degrees, and 6 degrees, respectively, as measured from the top thereof, so that there are observed four lines having the intervals of 6 mm apart each, calculated for the object point position. The images obtained by an image focusing system which have a magnification factor of one-eighth can be observed 0.7 mm apart each on a light receiving device R of Hamamatsu Photonix Inc., which is an integration of an image amplifier and CCD, as indicated by four lines 217 on monitor 216 shown FIG. 7. This performance is equal to approximately 25 vertical channel separations enough to separate and detect the images.

For a material of the divided filter 209, which has the films evaporated, is a glass having little wavelength dispersion, or having large $\nu d$, for example, BK-7 or the like. A large wavelength dispersion results undesirably in which the image lines are too thick for observation.

The four line image signals are appropriately converted to base signals for the respective samples by a detecting circuit 213 and a data processing unit 124, and is out to an output unit 215.

The same numbers and symbols given in the drawings substantially indicate identical parts or means.

As clearly seen from the description mentioned above, according to the present invention, first an image dividing means such as a mirror, prism, and lenses of different optic axes, are used for making a plurality of fluorescent light images, and each image is focused on a light reception device as passed through respective filters which identify different emission wavelengths of light to transmit. This technique can identify the signals from the multicolor-labeled DNA fragments at a high precision for a simultaneous measurement. This allows separation and detection or determination of the DNA base sequence at a high sensitivity and high accuracy.

Further, according to the present invention, the substantial light reception solid angle can be made larger by image division, not by time sharing. The lights from the multicolor fluorescent-labeled objects can be measured without decreasing the amount of light with use of a cylindrical convex lens.

In the fluorescence detection type electrophoresis apparatus of the present invention, no moving parts such as rotary filter are provided, thus eliminating anxiety of mechanical operation. Conventionally, manufacturing a large bandpass filter is difficult, but the present invention can make the filter small as a divided filter is provided near the focusing lens.

What is claimed is:

1. A fluorescence detection type electrophoresis apparatus, comprising:
   (i) a migration lane on which sample fragments labeled with fluorophore migrate electrophoretically;
   (ii) means for irradiating locally a predetermined portion to be irradiated with an excitation light for exciting said fluorophore, said predetermined portion being on said migration lane;
   (iii) optical means for focusing a fluorescent light image which is emitted from said fluorophore at said predetermined irradiated portion, on a plurality of focusing positions separated from each other, said optical means comprising:
      a) a focusing lens disposed on a predetermined distance from said predetermined irradiated portion; and
      b) an image dividing means disposed on an optical path from said predetermined irradiated portion to said focusing lens and makes said fluorescent light image visible as a plurality of virtual images positionally different from each other when said light image is seen from the focusing lens side;
   iv) a plurality of wavelength selection means disposed on the respective optical paths from said predetermined irradiated portion to said plurality of focusing positions, said respective optical paths lying separately from each other at the position of said wavelength selection means, and said plurality of wavelength selection means having transmission wavelength band different from each other; and
   v) a light detector for detecting with positional distinction each light amount of a plurality of fluorescent light images each of which had passed through each of said wavelength selection means and focused on each of said focusing positions.

2. A fluorescence detection type electrophoresis apparatus according to claim 1, in which the light detector is a two-dimensional detector.

3. A fluorescence detection type electrophoresis apparatus according to claim 1, which separates and detects DNAs or RNAs.

4. A fluorescent detection type electrophoresis apparatus comprising:
   i) a platelike migration lane on which a plurality of sample fragments migrate electrophoretically, said plurality of sample fragments being labeled respectively with a plurality of fluorophores having different maximum emission wavelengths from each other;
   ii) means for irradiating locally a predetermined portion to be irradiated with at least one laser beam for exciting said plurality of fluorophores, said predetermined portion being on said migration lane and having a bandlike shape with a longitudinal side perpendicular to the migration direction of said fragments;
   iii) optical means for focusing a bandlike fluorescent light image, which is emitted from the fluorophore at said predetermined irradiated portion, on a plurality of focusing positions separated from each other, said optical means comprising:
      a) a focusing lens disposed on a predetermined distance from said predetermined irradiated portion; and
      b) an image dividing means which is disposed on an optical path from said predetermined irradiated portion to said focusing lens and which makes said fluorescent light image visible as a plurality of virtual images positionally different from each other when said light image is seen from the focusing lens side;
   iv) a plurality of band-pass filters disposed on the respective optical paths from said predetermined irradiated portion to said plurality of focusing positions, said respective optical paths lying separately from each other at the positions of said band-pass filters, and each of said plurality of band-pass filters selecting a fluorescent light emitted from one of said fluorophores from the other fluorescent lights emitted from the other fluorophores with respect to the wavelength and transmitting the selected fluorescent light; and
   v) a light detector for detecting with positional distinction each light amount of a plurality of bandlike fluorescent light images which has passed through each of said band-pass filters and focused on each of said focusing positions, to thereby detect each of said plurality of sample fragments in passing through said predetermined irradiated portion.

5. A fluorescence detection type electrophoresis apparatus according to claim 4, in which said platelike migration lane is formed in a slab gel which is disposed between a pair of electrophoresis separation gel plates, the laser beam irradiation on said predetermined portion is directed from a side end surface side of the gel plates and penetrated through said slab gel of the electrophoresis separation gel plates, which is positioned in parallel with the electrophoresis separation gel plates, and a fluorescent light line image obtained by the laser irradiation is emitted along the path of the laser beam in the slab gel.

6. A fluorescence detection type electrophoresis apparatus according to claim 4, in which the image dividing means comprises a plurality of reflection mirrors arranged in parallel with an axis of a laser beam in the electrophoresis separation gel plates and in which a corresponding number of bandpass filters of different transmission wavelengths is provided on respective paths leading the fluorescent lights reflected by the reflection mirrors to focusing positions on said light detector which is a fluorescent light detector.

7. A fluorescence detection type electrophoresis apparatus according to claim 6, in which the plurality of the reflection mirrors are arranged on circumference of an ellipse having its center lying on said predetermined portion.

8. A fluorescence detection type electrophoresis apparatus according to claim 4, in which the image dividing means comprises at least a plurality if lenses of different optic axes or a lens divided into fragments of different optic axes said image dividing means being provided on a path on which fluorescent lights emitted from said predetermined portion propagate to the focusing position on the light detector.

9. A fluorescence detection type electrophoresis apparatus according to claim 8, in which an additional prism or mirror for dividing the fluorescent light image is provided on a path on which fluorescent lights emitted form said predetermined portion propagate to the focusing position on the light detector.

10. A fluorescent detection type electrophoresis apparatus comprising:
  i) a platelike migration lane on which sample fragments labeled with fluorophore migrate electrophoretically;
  ii) means for irradiating locally a predetermined portion to be irradiated with a least one laser beam for exciting said fluorophores, said predetermined portion being on said migration lane and having a bandlike shape with a longitudinal side perpendicular to the migration direction of said fragments;
  iii) a prism having an incidence plane on which the fluorescent light emitted from said fluorophore at the predetermined irradiated portion is made to be incident and having a plurality of light-outgoing planes;
  iv) a focusing lens which is disposed at a position capable of viewing said predetermined irradiated portion though said plurality of light-outgoing planes of said prism and by which said fluorescent lights outgoing from said plurality of light outgoing planes focus respectively on focusing positions different from each other to thereby form a plurality of respective bandlike image;
  v) a plurality of wavelength selection means disposed on the respective optical paths from said predetermined irradiated portion to said plurality of focusing positions, said respective optical paths lying separately from each other at the position of said wavelength selection means, and said plurality of wavelength selection means having transmission wavelength bands different from each other; and
  vi) a light detector for detecting with positional distinction each light amount of a plurality of bandlike fluorescent light images each of which has passed through each of said wavelength selection means and focused on each of said focusing positions.

11. A fluorescent detection type electrophoresis apparatus according to claim 10, wherein said wavelength selection means is disposed on the respective optical paths and disposed between said focusing lens and said light detector.

12. A fluorescent detection type electrophoresis apparatus according to claim 10, wherein said plurality of wavelength selection means is a multiplane filter having a plurality of light-outgoing planes, which is disposed between said focusing lens and said prism.

13. A fluorescence detection type electrophoresis apparatus according to claim 10, in which said platelike migration lane is formed in a slab gel which is disposed between a pair of electrophoresis separation gel plates, the laser beam irradiation on said predetermined portion is directed from a side end surface side of the gel plates and penetrated through said slab gel of the electrophoresis separation gel plates, which is positioned in parallel with the electrophoresis separation gel plates, and a fluorescent light line image obtained by the laser irradiation is emitted along the path of the laser beam in the slab gel.

14. A fluorescence detection type electrophoresis apparatus according to claim 10, in which the plurality of wavelength selection means is bandpass filters of individually different transmission wavelengths, said bandpass filters being provided on respectively corresponding paths of the divided image lights propagating out of the plurality of the light outgoing planes of the prism.

15. A fluorescence detection type electrophoresis apparatus according to claim 10, in which the fluorescence detection type electrophoresis apparatus is a multicolor fluorescence detection type electrophoresis apparatus, and the separation and detection sample for migrating in the electrophoresis separation plate is a multicolor-labeled sample.

16. A fluorescence detection type electrophoresis apparatus according to claim 10, in which at least one edge of the prism is in a plane including fluorescent light line images obtained as a result of laser beam irradiation to said predetermined portion and a center of the focusing position of the light detector, and is in parallel with the fluorescent light line images.

17. A fluorescence detection type electrophoresis apparatus according to claim 10, in which the prism is symmetric up and down with respect to a plane including fluorescent light line images obtained as a result of laser beam irradiation to said predetermined portion and a center of the focusing position of the light detector, and a vertex of the prism at the center is in parallel with the fluorescent light line images.

18. A fluorescent detection type electrophoresis apparatus comprising:
  i) a platelike migration lane on which a plurality of sample fragments migrate electrophoretically, said plurality of sample fragments being labeled respectively with a plurality of fluorophores having different maximum emission wavelengths from each other;
  ii) means irradiating locally a predetermined portion to be irradiated with at least one laser beam for exciting said plurality of fluorophores, said predetermined portion being on said migration lane and having a bandlike shape with a longitudinal side perpendicular to the migration direction of said fragments;
  iii) a cylindrical convex lens converging a fluorescent light emitted from said fluorophore at said predetermined irradiated portion, in a width direction of said predetermined irradiated portion of bandlike shape;
  iv) a prism having an incidence plane on which the fluorescent light transmitted through said cylindrical convex lens is made to be incident and having a plurality of light-outgoing planes;
  v) a cylindrical concave lens diverging a fluorescent light outgoing from said plurality of light-outgoing plane of said prism, in a width direction of said predetermined irradiated portion of bandlike shape;
  vi) a focusing lens which is disposed at a position capable of viewing said predetermined irradiated portion of bandlike shape through said cylindrical concave lens, said prism and said cylindrical convex lens and which focuses said fluorescent lights outgoing from said plurality of light-outgoing planes respectively on focusing positions different from each other to thereby form respectively a plurality of bandlike images;

vii) a plurality of band-pass filters disposed on the respective optical paths from said predetermined irradiated portion to a plurality of said focusing portions, said respective optical paths lying separately from each other at the positions of said band-pass filters, and each of said plurality of band-pass filters, and each of said plurality of band-pass filters selecting a fluorescent light emitted from one of said fluorophores from the other fluorescent lights emitted from the other fluorophores with respect to the wavelength and transmitting the selected fluorescent light; and viii) a light detector for detecting with positional distinction each light amount of a plurality of bandlike fluorescent light images which has passed through each of said band-pass filters and focused on each of said focusing positions, to thereby detect each of said plurality of sample fragments in passing through said predetermined irradiated portion.

19. A fluorescence detection type electrophoresis apparatus according to claim 18, in which said platelike migration lane is formed in a slab gel which is disposed between a pair of electrophoresis separation gel plates, the laser beam irradiation on said predetermined portion is directed from a side end surface side of the gel plates and penetrated through said slab gel of the electrophoresis separation gel plates, which is positioned in parallel with the electrophoresis separation gel plates, and a fluorescent light line image obtained by the laser irradiation is emitted along the path of the laser beam in the slab gel.

20. A fluorescence detection type electrophoresis apparatus according to claim 18, in which said plurality of bandpass filters is a divided multiplane filter, by which the fluorescent light image is divided.

21. A fluorescence detection type electrophoresis apparatus according to claim 20, in which the divided multiplane filter is provided between the cylindrical convex lens and said focusing lens.

22. A fluorescence detection type electrophoresis apparatus according to claim 21, in which planes of the divided multiplane filter have areas sized so that amounts of the fluorescent lights passing them can be substantially equal.

23. A fluorescence detection type electrophoresis apparatus according to claim 18, in which the cylindrical convex lens comprises a plurality of divided cylindrical convex lenses, by which the fluorescent light image can be divided.

24. A fluorescence detection type electrophoresis apparatus according to claim 18, in which a slit is provided in parallel with fluorescent light line images between an emitting point of the fluorescent light line images and a cylindrical convex lens to cut out upper and lower parts of the fluorescent lights emitted from the emitting point higher or lower than specific angles.

25. A fluorescence detection type electrophoresis apparatus according to claim 24, in which a width of the slit is made narrower than an interval of virtual object positions.

* * * * *